(12) United States Patent
Kencl et al.

(10) Patent No.: US 8,856,940 B2
(45) Date of Patent: Oct. 7, 2014

(54) PROCESSING OF DATA INFORMATION IN A SYSTEM

(76) Inventors: Lukáš Kencl, Prague (CZ); Martin Loebl, Prague (CZ); Jenny Blamey, Santiago (CL)

( * ) Notice: Subject to any disclaimer, the term of this patent is extended or adjusted under 35 U.S.C. 154(b) by 995 days.

(21) Appl. No.: 12/670,908

(22) PCT Filed: Jul. 2, 2008

(86) PCT No.: PCT/CZ2008/000076
§ 371 (c)(1),
(2), (4) Date: Jan. 27, 2010

(87) PCT Pub. No.: WO2009/015616
PCT Pub. Date: Feb. 5, 2009

(65) Prior Publication Data
US 2010/0205676 A1    Aug. 12, 2010

(30) Foreign Application Priority Data
Jul. 30, 2007    (CZ) .................................... 2007-509

(51) Int. Cl.
*G06F 21/00* (2013.01)
*H04L 29/06* (2006.01)
*G06F 21/62* (2013.01)
*G06F 19/00* (2011.01)

(52) U.S. Cl.
CPC .......... *H04L 63/145* (2013.01); *G06F 21/6254* (2013.01); *G06F 19/3437* (2013.01)
USPC ......................................................... 726/26

(58) Field of Classification Search
USPC .............. 726/26; 713/160; 380/239; 382/128
See application file for complete search history.

(56) References Cited

U.S. PATENT DOCUMENTS

| | | | |
|---|---|---|---|
| 7,802,257 B1* | 9/2010 | Pariente ........................ | 718/104 |
| 2003/0081776 A1* | 5/2003 | Candelore ..................... | 380/200 |
| 2008/0005264 A1* | 1/2008 | Brunell et al. ................ | 709/217 |

OTHER PUBLICATIONS

International Search Report (Form PCT/USA/210) and Written Opinion of the International Search Authority (Form PCT/ISA/237) mailed Mar. 23, 2009 in corresponding PCT/CZ2008/000076
Ponce, José Zamora, et al., "Packet Content Anonymization by Hiding Words," *IEEE INFOCOM* [Online], Apr. 25, 2006, three (3) pages, XP002517637, Retrieved from the Internet: URL:http://www.ieee-infocom.org/2006/Posters/1568980924_Packet%20Content%Anonymization.pdf.

(Continued)

*Primary Examiner* — Matthew Smithers
(74) *Attorney, Agent, or Firm* — Buchanan Ingersoll & Rooney PC

(57) ABSTRACT

Data information, represented by electric or wave signals, or data information within the artificial or natural databases and storage media, such as for example DNA (Deoxyribonucleic Acid), encoded as a sequence of symbols, is, for the purpose of its concealing and simultaneously preserving its select local data information segments, partitioned within a physical medium, such as especially computer hardware, physical communication channel, physical storage medium or biological material, into short overlapping data segments. The studied local data information segments are contained within the short segments in their entirety. these partitioned short segments constitute the first group and to at least one short segment of the first group, data, encoded as selected symbols, are prepended or appended, to the symbols of the short segments of the first group. The resulting mixture of segments is interconnected into a sequence of data. The entire process may be repeated multiple times.

13 Claims, 1 Drawing Sheet

(56) References Cited

OTHER PUBLICATIONS

Kargupta, Hillol, et al., "On the Privacy Preserving Properties of Random Data Perturbation Techniques," *Data Mining,* 2003. ICDM 2003. Third IEEE International Conference on Nov. 19-22, 2003, Piscataway, NJ, USA, IEEE, Nov. 19, 2003, pp. 99-106, XP010673159, ISBN: 978-0-7695-1978-4.

* cited by examiner

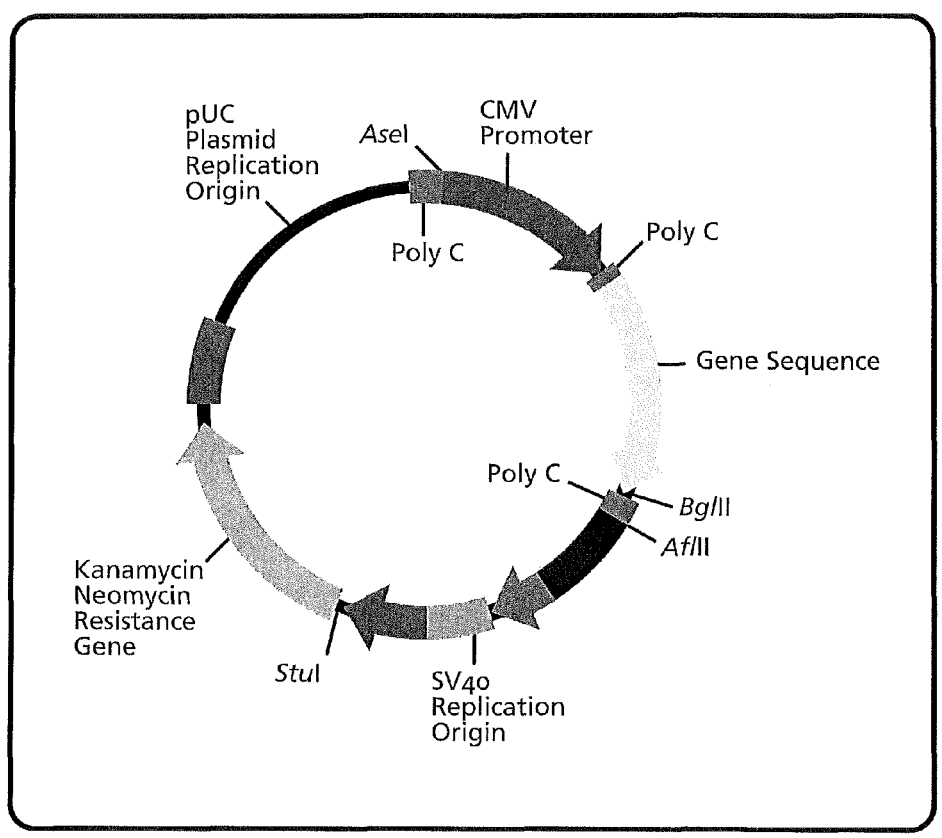

PROCESSING OF DATA INFORMATION IN A SYSTEM

TECHNOLOGY AREA

The invention is concerned with processing of information for the purpose of its masking and for protection of content of sensitive information, while preserving only its part, the studied local data information, within a system containing at least some information. The system is composed of elements and of information-sharing among the elements. All information is generally understood as data information, which is contained within natural databases, for example the genetic data information stored in DNA and bonded to chromatin threads, or data information stored in artificial databases and storage media.

Data information is also represented by electrical or wave signals, such as in particular datagrams, packets or traces passing through one or more nodes within the networks of the Internet in a given time period, or data within search engines or data generated by operating systems and related applications, or data logged by for example a node of a communication network or the exchanged information contained within the networks of operators. Data is generally encoded as a sequence of characters selected out of a group of letters, digits or arbitrary characters. A system is characterized by at least one sequence.

BACKGROUND OF THE INVENTION

By elements we understand for example Internet users, various workgroups of one company or government institution, users of the same application, for example of the same computer program or information system, cells in a biological system, for example in a multicellular organism, or microorganisms or viruses that communicate or interchange fragments or total DNA, as in gene transfer. Elements may also be intermediaries of information sharing, such as communication channels or nodes, elements may also be groups of elements or subsystems. Data information about an element may for example be the genetic information of a cell or the electric signals representing the state of an operating system at a certain point in time or for example the electric signals or the wave signals representing the identification data stored in artificial databases, for example storing age and address. By information sharing we understand for example Internet communication or aggregate communication data (e.g. a trace of data exchange among multiple users as stored by e.g. an intermediate communication network node) or exchange of information contained within operator networks or publication of aggregate data about for example network searches. By sharing of information in biological systems we understand for example processing of various signals, or of genetic information fragments, contained in genomic DNA, by cells, or by parts of DNA of a single cell.

Common statistical methods gather information about elements and information shared by elements without the private content removed. These methods assume that the information is gathered by an authority that is generally trusted not to abuse the gathered information and also to protect it from malicious attacks. This assumption is unrealistic: the individual elements often have no reason to trust the information-gathering authority. Therefore they do not make the information available and the statistical analysis is not possible. Sometimes, protection of access to sensitive information during analysis or study by a third party is solved by bi-partial legal contracts and considerable sanctions in the case of information leak or abuse. The disadvantage of such approach is the considerable work expenditure, poor scalability, complicated or impossible access for further parties, complicated and costly control and enforcement, complicated and costly security protection and considerable ineffectiveness (in particular against leaks caused by own personnel).

However, there exist important techniques concerning systems that only need partial information. An example of such technique is intrusion detection in Internet communication, where presence of a virus is indicated by the Internet communication containing a short segment present in a database of malicious segments. Danger of a different threat may be indicated by frequent repetition of the same short segment within Internet communication.

For techniques concerning systems that require only partial data information, short segments of the original data information are important, which we denote as local data information segments. We denote as collection of local data information segments any unordered group of multiple local data information segments. The above reasoning motivates the need to process the original data information—encoded as sequence of symbols, so that its content is concealed yet the relevant collection of local data information segments is preserved.

The processed data information containing the collection of local data information segments could be shared and would enable analysis and corrections of the system and it would encourage mutual communication among elements. A proposal for processing of data information was presented in the work: Lukas Kencl, Jose Zamora, Martin Loebl, "Packet Content Anonymization by Hiding Words", *Demo at IEEE INFOCOM,*, Barcelona, Spain, April 2006, using random permutations of a collection of short overlapping data segments. However, it was shown later that this technique does not lead to concealing the original data information.

From biology we know that a large fraction of the eukaryotic genome is composed of DNA sub-segments, which are repeating many times exactly, or with slight alterations. In computational biology this phenomenon is identified as the main obstacle of the current methods in reconstructing longer segments of DNA out of a known set of shorter overlapping segments. The reason is that if the set contains a large amount of shorter segments with repeating initial or terminal sub-segments, there exist an uncontrollable number of possible variations of reconstruction of the longer segments which would be consistent with the analysis of overlaps.

BRIEF SUMMARY OF THE INVENTION

Data information, needed for solving a number of problems of various systems, is, in particular due to its potential abuse, often not available. Its unavailability has motivated us to consider the problem of processing data information so that the original content would be concealed but the local data information segments, which would be the objects of the system study, would remain preserved.

The discussed inadequacies, in particular concerning the potential abuse of information, are resolved by processing of the data information, represented by electric or wave signals, or of the data information within natural or artificial databases and storage media, for the purpose of concealing and protecting the content of sensitive data information and simultaneously preserving its select part, the studied local data information segments, in a system containing at least one segment of data information, where the original data information is encoded as a sequence of characters selected out of a group of letters, digits or arbitrary characters, where the processing rests in splitting the original data information within a physical medium, such as for example computer hardware, physical communication channel, physical storage medium or biological material, into short overlapping data segments, where the length of the split segments is at least as long or longer than the length of the studied local data information segments and the studied local data information segments are contained in the short segments in their entirety, these split short segments constitute a first group of segments, and to at least some short segments of the first group data, encoded as select symbols before or after the symbols of the short segments of the first group, are added, where the symbols selected for augmentation and their sequence is either identical or different and the resulting mix of the original and the augmented segments constitutes a second group and the segments of the second group are interconnected into a data sequence.

It is advantageous to process these interconnected segments of the second group again according to the preceding method, and the resulting new second group is again interconnected into a data sequence and this procedure may be repeated multiple times.

Data information processed in this manner, that is data sequences and/or masked data sequences, created for example by its own system using repeating data sub-segments, as is known for example in the area of biology, may be used for studying the relevant system and for analyzing the data concerning the local information segments. For instance, presence of specific short segments, relative frequency of occurrence of identical segments or their dependence on time may be studied.

Data sequences processed in this manner according to the invention, and/or masked data sequences created for example by its own system using repeating data sub-segments, may be further used for construction and coordination of complex systems.

Data sequences processed in this manner and/or masked data sequences created for example by its own system using repeating data sub-segments may be used for data information checking, that is for example for processing of logs, traces, footprints or instances of operating systems or computer applications, from the point of security, correctness, trustworthiness. Or it may be used for statistical analysis, for example of frequently used instructions or blocks of data, for example to establish safe communication or collaboration, to migrate or replicate to another computing device or processor, to copy to another device or medium for the purpose of storage or to study its behavior in dependence on time.

Data sequences processed in this manner and/or masked data sequences created for example by its own system using repeating data sub-segments may safely be used for example for sharing, publishing, sale, exchange and analysis of network data and of search engine data, or for instance of traces, footprints or instances of operating systems, computer applications or of recorded communication and interaction.

Data sequences processed in this manner and/or masked data sequences created for example by its own artificial, biological or otherwise system using repeating data sub-segments may be used for a study of the system with the goal of understanding its dynamic evolution and of detection, prevention, use or isolation of an attack, infection or of another phenomenon observable in the system.

An advantageous manner of use rests in that within at least one processed and/or masked data sequence, represented as a sequence of symbols, groups of repeating data sub-segments are traced and/or of their location within the sequence and/or their continuous changes in time, and/or their changes in location in the sequence, where these changes may be triggered naturally or artificially, This manner of tracing is useful for diagnostics of abnormal behavior of the mechanism of concealing data information by using groups of repeating data sub-segments in the observed part of the system, and for coordination of the system, resting in prevention of system flaws, for example of illnesses in a biological system, caused by abnormal behavior of the mechanism of information concealing using the groups of repeating data sub-segments, within a part of the system.

A long-term observer of the data sequence processed according to the invention and/or of the masked data sequence, created for example by its own system by using repeating data sub-segments, may, after some duration of observation, be able to reconstruct parts of the original data information.

Therefore, the described modification and construction of the system is advantageously performed further according to the invention, which rests in that groups of repeating data sub-segments contained within at least one processed and/or masked data sequence, represented as a sequence of symbols, are being continuously modified by for example adding further data, encoded as symbols, to the repeating data sub-segments to their beginnings and/or ends, and/or a group of data, encoded as symbols, may be replaced within these sub-segments and/or the data sub-segments may be moved to another location in the processed data sequence and/or further data sub-segments, already contained in the sequence, may be randomly inserted into the processed data sequence.

This construction and modification may be performed by each element of the system according to the selected technological process on its own.

Furthermore, the invention concerns the method of construction of an artificial, biological or otherwise system using new information, resting in that the short segments containing the collection of local data information segments from the new data information are pre-pended and/or appended with data sub-segments from the collection of the repeating data sub-segments of the constructed data sequence, and the resulting collection of data segments is randomly inserted into at least one constructed processed and/or masked data information segment.

BRIEF DESCRIPTION OF THE DRAWING

FIG. 1 is a drawing of a plasmid according to a preferred embodiment of the present invention.

DETAILED DESCRIPTION OF THE INVENTION

When observing the behavior of biological systems we have conceived the idea that groups of repeating data sub-segments in the genome at the DNA level may have a protective, concealing function. They seek to prevent that longer segments of DNA of individual cells—elements of a biological system—be easily reconstructed from knowing the shorter segments.

Furthermore, we conceived the idea to use the described, empirically observed difficulties of reconstruction of a sequence of symbols, which contains groups of repeating sub-segments out of a collection of its overlapping segments, to propose a mechanism how to process the data information encoded as a sequence of symbols so that the original data information is concealed, but a collection of local data information segments—short data segments—remained intact for statistical analysis and other important tasks concerning systems.

Some of these short data segments may be found in for example a database indicating a computer virus presence. In computational biology a correlation has also been observed between the atypical evolution of groups of repeating short segments within DNA and particular diseases, for example diabetes or schizophrenia.

DNA is generally regarded as repository of genetic information. It occurred to us that DNA, which contains groups of repeating sub-segments, acts as processed masked information. A collection of local data information segments—short segments of the DNA sequence, is available to other cells within a biological system, being it a multicellular system or microorganisms or viruses, interacting with each other or with a multicellular system, for observations. It occurred to us that this DNA behavior may be used for studying and construction of biological systems, as well as for construction, studying and coordination of other systems.

The most important contribution of processing of information according to the invention is concealing of the original information, encoded as a sequence of symbols, and thus concealing the content and meaning of the original information, while the relevant collection of the local data information segments is preserved. The elements of the system do not have to fear reconstruction of the original data information or abuse when handing over processed data information or data sequences. Various variations of the method of the invention, which are available to every element, are used for processing the data information. Using these different variations of the method, the elements process their own original data information themselves and then make it available for studying and corrections of the system.

The advantage of processing of data information according to the invention is enabling various applications concerning the processed data information within systems. This includes for example studying and modeling of behavior and communication of the communication network users on the basis of the processed data sequence—the communication record (including its processed content), which can be advantageously used for example for creation of targeted advertising, for creation of coaching applications, for analysis, training and improving effectiveness of individuals and organizations or for optimizing operations or detection of faults or attacks within the Internet network, where in all these cases the presence of sensitive data, contained in the unprocessed data information, would prevent the use of such application, especially if developed, operated or used by another party. Behavior of users of automated search engines can be studied and modeled by using the processed data information—search records, and the search engine operators may optimize the search engine operation and the targeting of advertisements on the basis of the obtained data. Records of communication of network subscribers and of searches of search-engine users may, in the form of the processed data sequence according to the invention, also be offered commercially for sale to third-parties, published or exchanged among network or search-engine operators, because the high computational complexity of reconstruction of the original (unprocessed) data information prevents abuse of sensitive information about subscribers or users. Data information processed according to the invention may also be used for example for making databases of medical or biological records accessible for the purpose of research or development of novel medicaments or of novel healing or diagnostic methods or of modeling individual behavior. Furthermore, it may also be used for sharing data sequences from recording media (such as sound or video-camera systems) in the cases of security protection by another party or when obliged to share data with government security authorities. Processed data information may also be advantageously used for verifying security, correctness or trustworthiness of individual instances of operating systems or of applications running on top of them, without revealing sensitive data contained within these systems.

Furthermore, the invention enables such construction and coordination of systems that lead to improved system functionality. In a system where the processed and/or masked data information of each element is freely available and shared by the entire system, complex coordination is possible that would enable prevention of spreading of an adverse phenomenon, such as for example viruses in the Internet network, or as is for example coordination of systems of cells in a multicellular organism, where the shared masked genetic information of each cell is contained in its DNA. In the course of studying the relevant local data information segments and groups of repeating data sub-segments and their changes and/or changes in their position in over time, it is possible for example to carry out diagnostics and fault prevention in a system or its parts, and it is also possible to detect or predict global defects of the system caused by defects of the mechanism carrying out the actual masking of information. It is for example possible to judge the health state of biological systems.

When inserting novel data information into a constructed data sequence, faster positive result and greater stability of the final product, that is for example greater resistance to auto-immune reactions within biological systems, may be achieved by processing the novel data information according to the invention.

IMPLEMENTATION EXAMPLES

Example 1

Processing of Data Information Communicated over the Internet to Enable Statistical Analysis and Study of the Internet Within the networks of the Internet, data information is represented by electric or wave signals, passed over in the form of datagrams or packets. Datagrams or packets are coded as sequences of symbols of certain length, determined by the used protocol. Packets consist of a header, containing the source and destination address and other control data, and of a payload (content), which contains the actual communicated data. Data communicated between two or more users may be partitioned into multiple packets over the Internet, which may neither travel across the Internet contiguously after each other nor over the same route. A record of packets passing through one or more nodes of the Internet in a given time interval is usually called a trace. This trace, or only the part of it without the headers, represents the communicated—shared data information over the Internet and constitutes the input—the original data information encoded as a sequence of symbols. A study of such trace may detect a passed computer virus by comparison with a virus database, or a rapidly spreading Internet worm by a sudden frequent occurrence of particular short segments. However, the trace also contains communication of private nature that the network operator does not want to or is not allowed to keep record of, make accessible or publish. Nevertheless, for the purpose of detecting a dangerous virus a collection of local data information—short segments—may suffice.

The processing of the input, the original data information, encoded as sequence of symbols, using one of the variations of the method of invention, will process the trace into a processed data sequence coded as a sequence of symbols, which contains the collection of the local data information segments from the original trace, but the original trace is provably computationally hard to derive from it, especially as the processed trace contains groups of repeating data sub-segments. The processing of the data information according to this invention may be for example carried out according to the following method alternative.

This alternative is described for the case when it is desirable to preserve all the local data information segments of given length. But one may proceed analogously also in the case when the local data information segments to be preserved are different, for example not of the same length. Let us thus denote as k the length of the local data information segments that we want to preserve after the processing. We describe this alternative of the method using procedures operating on sequences of symbols that encode data information.

We begin with a description of several simple procedures, out of which the method is finally composed. A cyclic sequence denotes a sequence-succession of symbols where the beginning and end are aligned.

Procedure $S1(s,o,z,Z)$: its input is a cyclic sequence s, and the parameters of the length of segments are the numbers $o,z,Z$ where the length of the local data information segment k is smaller or equal to o, which is smaller or equal to z, which is smaller or equal to Z. This procedure consists of the following steps. First, the sequence s is partitioned into segments $B1, \ldots, Bm$ so that the length of each Bi is randomly selected out of the interval $(z,Z)$. Segments $B1, \ldots, Bm$ constitute the first group. Further on, to the beginning of each segment, the end sub-segment of length o of the preceding segment is pre-pended. Furthermore, to the end of each thus created segment a sub-segment, containing one or two symbols randomly selected of the sequence s, may be appended. Segments processed in this manner constitute the second group. Finally, segments of the second group are ordered into sequence in a random order.

Procedure $S2(s, z, Z)$: the input is a cyclic sequence s and the segments length parameters are the numbers $z,Z$. This procedure consists of the following steps.

Firstly, the sequence s is partitioned into segments $B1, \ldots, Bm$ so that the length of each segment Bi is randomly selected out of the interval $(z,Z)$. Segments $B1, \ldots, Bm$ constitute the first group. Further on, to the beginning of each segment, a copy of the entire preceding segment is pre-pended. Alternatively, for example only a significant final portion of the preceding segment may be appended. Alternatively, to each thus created segment one may also append a short segment selected out of the sequence s such that the end portion of this newly created segment is repeated within the collection of segments. Segments processed in this manner constitute the second group. Finally, segments of the second group are ordered into sequence in an order that can be described as: Every segment of the first group appears once as the initial and once as the terminal segment of some segment of the second group. Therefore one can describe this ordering by a bijection (permutation) p of the segments of the first group such that the segment of the second group that ends with a segment Bi of the first group is followed in the order by a segment of the second group initialized by the sub-segment $Bp(i)$ of the first group. In an alternative implementation of the method, significant portions of the segments of the first group are subject to the process instead of the segments themselves. For the ordering one may use an arbitrary permutation for which a sufficient number of indices (for example 10%) i satisfies the condition $p(p(i)-1)=i+1$.

Procedure $S3(s,o,z,Z)$: the input is a cyclic sequence s, and the parameters of the length of segments are the numbers $o,z,Z$. Suppose that sequence s is in the form of the output of procedure S2, i.e. the sequence s can be written as $B1B2Bp(2)B(p(2)+1) \ldots B(r-1)Br$, where r is the index satisfying $p(r)=1$. First we describe how the sequence s is partitioned. For the description it suffices to describe the splits that will be carried out within the s sequence. At both occurrences (within the sequence $s=B1B2Bp(2)B(p(2)+1) \ldots B(r-1)Br$) of each Bi of the first group we carry out identical splitting of the sequence s so that the segment Bi is partitioned into two sub-segments, where the initial sub-segment should have length at least o. The segments of the thus partitioned sequence s then constitute a new first group. Further on, to every segment of the new first group the terminal sub-segment of length o of the preceding segment is pre-pended. Furthermore, to every newly created segment, a segment of short length randomly selected out of sequence s may be appended. Segments processed in this manner constitute a new second group. Finally, segments of the new second group are ordered into sequence in random order.

The two principle alternatives of the method of processing of data information may now be described as $S3(S2(S1\char`\^3, (s,k,k,3k/2),k,3k/2),k,k,3k/2)$ and $S3(S2(s,k,3k/2),k,k,3k/2)$, where the cyclic sequence s is created out of the input sequence by aligning its end and beginning, k is length of the local information segment that is desirable to preserve and $S1\char`\^3$, denotes three applications of procedure S1, but it is also possible to combine the procedures using a number of other means, for example it is possible to choose a different number of applications of procedure S1 than three.

Every element of the system may very easily process its data information using these variations and make it available to others, as reconstruction of the sensitive original data information—encoded as sequence of symbols, on the basis of the processed data sequence is provably computationally hard, because for reconstructing longer segments there exists a large number of feasible variations consistent with the analysis of the processed sequence of symbols.

The created processed data sequence allows studying a collection of local information segments of the original trace, for example a study of the approximate frequency of occurrence of particular patterns-short segments, indicating the presence of a virus. The mechanism also enables trace publishing, allowing access to or exchange of traces among those elements of the system (operators, users) that may not trust each other.

Example 2

Coordination of a System of Elements—Users of Operating Systems

As state of an operating system we denote a collection of configurations of a computer that manage the resources present in the computer, such as for example a processor, memory, hard disk, program execution, applications, etc.

Among other tasks the operating system monitors the status of individual applications running on top of it and of files stored on the hard disk. At an arbitrary point in time the operating system is in some entirely recordable state, represented by electrical signals and records on the storage media, which all together we may denote as a footprint of an operating system. The footprint contains for example the state of all applications running on top of and managed by this operating system, and the state and contents of all files managed by the given operating system. Such footprint of an operating system at a given point in time is generally encoded as a sequence of symbols. Within the system this sequence of symbols constitutes the encoding of the original data information of an element-user at the given point in time. The system is created in the following manner: the elements-users process the footprint of their own operating system for example according to the alternative described in the first example. An element-user may then make the resulting processed data sequence available at an accessible location, for example on his/her own website, encoded as a sequence of symbols.

Analogously as the state of the operating system changes with time, its footprint and its processed footprint also change. The processing may be achieved by for example repeated re-processing of the entire footprint—always within a certain time interval, for example according to the alternative described in the first example. It is also feasible to focus only on those data a that differ over time in comparison with the previous footprint-s.

When constructing the new processed footprint v these segments a may be inserted into the constructed data sequence v for example in the following manner: the newly inserted data are first processed for example according to the alternative described in the first example. Repeating data sub-segments out of the groups of repeating sub-segments already contained in the constructed data sequence v are pre-pended and/or appended to every short data segment out of the thus created local data information segments or to the entire new data segment if the previous processing is not carried out. Segments thus constructed are then randomly inserted into the constructed data sequence v.

The elements—users make the processed data sequence v, encoded as a sequence of symbols, available at a freely accessible place, for example at their web site, or at a place with access limited to for example only some other elements—users. These shared processed data sequences serve for studying the system as well as the individual elements by examining the data concerning the local data information segments within the footprints (for example the occurrence of specific short data segments, relative frequency of identical data segments or its change over time). Such a study may serve for example for verification of the system or of the elements—users from the perspective of security, correctness, trustworthiness or for statistical analysis e.g. of frequently used instructions or blocks of data. That may be used for example to establish secure communication or cooperation among elements, during their migration or replication to another computing equipment or processor or when being copied to other equipment or media for the purpose of storage. It may also be used for construction and study of the entire system, for example with the purpose of understanding its dynamic evolution and detecting and isolating a virus or an infection in the system. Examples of systems that function in that manner are biological systems.

Example 3

For insertion of new genetic data information, for example to construct a fusion protein product, into cells, genetically created bacterial plasmids and viral vectors are used. By processing the genome using plasmids one may create transformed cell lines.

For expression of specific proteins, a specific plasmid may be used, constructed out of a pUC plasmid basic structure. Into this plasmid, a replication origin, a promoter, a gene that confers resistance to multiple antibiotics, several enzyme restriction sites, and the site to incorporate the genetic data information that one would like to insert, have to be incorporated.

The created plasmid and the transcription and expression of the relevant protein from the genetic data information in a cell, is more stable, if the promoter is preceded by a short repeating sub-segment poly C, followed by the promoter, then another sub-segment of poly C, and then the genetic data information (a gene, for example) that we would like to insert into the newly constructed plasmid. Finally, at the end, it is followed by another sub-segment of poly C. Such method of inserting the repeating sub-segments leads to greater stability of the relevant plasmid and of transcription and expression of the relevant protein. If one desires to produce the relevant protein in eukaryotes, it could be advantageous to use at the end a sub-segment of poly A, instead of a sub-segment of poly C. FIG. 1 shows one of many possible examples

The invention claimed is:

1. A method for processing data information in a system, for the purpose of concealing and protecting data information content, while simultaneously preserving part of the data information, segments of processed data information being contained within a system containing at least one data information, represented by electrical or wave signals or by data information existing in nature or in artificial databases or in storage media, where the processed data information is represented as a sequence of symbols selected out of a set consisting of characters, digits, or other arbitrary symbols, comprising the steps of:

partitioning the data information within a physical media or a machine, into short overlapping data information segments together having a number of symbols defining a size of the short overlapping data information segments, where the size of the short overlapping data information segments is at least identical or greater than a size of local data-information segments being studied, and wherein the local data information segments being studied are entirely contained within the short overlapping data information segments, these short overlapping data information segments constituting a first group;

modifying at least one short overlapping data information segment of the first group by pre-pending before or appending after at least one selected symbol, while said at least one selected symbol and a sequential order of said at least one selected symbol may repeat or differ, and an obtained mixture of the short overlapping data information segments and said modified at least one short overlapping data information segment of the first group constitutes a second group;

connecting segments of the second group into a sequence of data information;

partitioning the connected segments of the second group into short overlapping data information segments together having a number of symbols defining a size of the short overlapping data information segments, where the size of the short overlapping data information segments is at least identical or greater than a size of local data-information segments being studied, and wherein the local data information segments being studied are entirely contained within the short overlapping data information segments, these partitioned short overlapping data information segments constituting a new first group;

modifying at least one short overlapping data information segment of the new first group by prepending before or appending after at least one short data-information segment of the new first group at least one selected symbol, and an obtained mixture of the short data-information segments of the new first group and the modified short data-information segments of the new first group constituting a new second group;

connecting the new second group into a sequence of data information;

partitioning the connected segments of the new second group into short overlapping data information segments together having a number of symbols defining a size of the short overlapping data information segments, where the size of the short overlapping data information segments is at least identical or greater than a size of local data-information segments being studied, and wherein the local data information segments being studied are entirely contained within the short overlapping data information segments, these partitioned short overlapping data information segments constituting another new first group; and modifying at least one short overlapping data information segment of the another new first group by prepending before or appending after at least one short data-information segment of the another new first group at least one selected symbol, and an obtained mixture of the short data-information segments of the another new first group and the modified short data-information segments of the another new first group constituting another new second group to extend collection of repeating data-information sub-segments in output concealed data information.

2. The method of claim 1 further comprising the step of using the concealed data information that is the output data information sequence created by a system using repeating data sub-segments, for studying the system and elaborating particulars concerning the local data information segments.

3. The method of claim 1 further comprising the step of using the concealed data information that is the output data information sequence created by the system using repeating data-information sub-segments, for construction and coordination of complex systems.

4. The method of claim 3, wherein groups of repeating data-information sub-segments contained in at least one concealed and/or masked data information sequence are being modified by appending and/or pre-pending further data, encoded as symbols, to the repeating data-information sub-segments, and/or a group of symbols is exchanged in these data-information sub-segments and/or the data-information sub-segments are relocated to another position within the data information sequence and/or further data-information sub-segments, already contained within the data-information sequence, are randomly inserted into the data-information sequence.

5. The method of claim 3, further comprising the step of using a new data information sequence, wherein data-information sub-segments out of the groups of repeating data-information sub-segments of a constructed data sequence are pre-pended and/or appended to the short data-information segments containing a collection of local data-information segments of the new data information sequence, and the resulting group of data-information segments is randomly inserted into at least one constructed data sequence.

6. The method of claim 2 further comprising the step of using the concealed data information, for inspecting operating systems or computer applications with respect to security, correctness, trustworthiness or statistical analysis on the basis of local data information.

7. The method of claim 2 further comprising the step of using the concealed data information, for processing of data in networks and search engines.

8. The method of claim 2 further comprising the step of using the concealed data information for a study of a system with the purpose of understanding a system evolution and of identification, prevention, use or isolation of an attack, infection or other observable phenomenon in the system.

9. The method of claim 2 further comprising the step of using the concealed data information, wherein groups of repeating data information sub-segments and/or a position of repeating data information sub-segments within the data sequence and/or transient changes in time of repeating data information sub-segments and/or changes in a positioning of repeating data information sub-segments within the data sequence are traced, where these changes may be induced in nature or artificially.

10. The method of claim 9 further comprising the step of diagnosing abnormal behaviour of masking a data information sequence, by the system using groups of repeating data sub-segments, within a studied part of a system.

11. The method of claim 9 further comprising the step of coordinating a system, which rests in preventing faults and/or diseases of the system, caused by abnormal behaviour of masking a data-information sequence by the system using groups of repeating data-information sub-segments in part of the system.

12. A method for processing data information in a system, for the purpose of concealing and protecting data information content, while simultaneously preserving part of the data information, segments of processed data information being contained within a system containing at least one data information, represented by electrical or wave signals or by data information existing in nature or in artificial databases or in storage media, where the processed data information is represented as a sequence of symbols selected out of a set consisting of characters, digits, or other arbitrary symbols, comprising the steps of:

partitioning the data information within a physical media or a machine, into short overlapping data information segments together having a number of symbols defining a size of the short overlapping data information segments, where the size of the short overlapping data information segments is at least identical or greater than a size of local data-information segments being studied, and wherein the local data information segments being studied are entirely contained within the short overlapping data information segments, these short overlapping data information segments constituting a first group;

modifying at least one short overlapping data information segment of the first group by pre-pending before or appending after at least one selected symbol, while said at least one selected symbol and a sequential order of said at least one selected symbol may repeat or differ, and an obtained mixture of the short overlapping data information segments and said modified at least one short overlapping data information segment of the first group constitutes a second group;

connecting segments of the second group into a sequence of data information;

partitioning the connected segments of the second group into short overlapping data information segments together having a number of symbols defining a size of the short overlapping data information segments, this partitioning is carried out in such manner that, together with the partitioning of the connected segments of the first group, they result in an increased number of collections of at least three repeating data-information sub-segments being present within all segments of the output concealed data information, where the size of the short overlapping data information segments is at least identical or greater than a size of local data-information segments being studied, and wherein the local data information segments being studied are entirely contained within the short overlapping data information segments, these partitioned short overlapping data information segments constituting a new first group;

modifying at least one short overlapping data information segment of the new first group by prepending before or appending after at least one short data-information segment of the new first group at least one selected symbol, and an obtained mixture of the short data-information segments of the new first group and the modified short data-information segments of the new first group constituting a new second group;

connecting the new second group into a sequence of data information, this connecting is carried out in such manner that, together with the partitioning of the connected segments of the new first group, they result in an increased number of collections of at least three repeating data-information sub-segments being present within all segments of the output concealed data information;

partitioning the connected segments of the new second group into short overlapping data information segments this partitioning is carried out in such manner that, together with the partitioning of the connected segments of the first group and together with the partitioning of the connected segments of the second group and together with connecting of the new second group into a sequence of data information, they result in an increased number of collections of at least three repeating data-information sub-segments being present within all segments of the output concealed data information, together having a number of symbols defining a size of the short overlapping data information segments, where the size of the short overlapping data information segments is at least identical or greater than a size of local data-information segments being studied, and wherein the local data information segments being studied are entirely contained within the short overlapping data information segments, these partitioned short overlapping data information segments constituting another new first group; and modifying at least one short overlapping data information segment of the another new first group by prepending before or appending after at least one short data-information segment of the another new first group at least one selected symbol, and an obtained mixture of the short data-information segments of the another new first group and the modified short data-information segments of the another new first group constituting another new second group connecting the segments of the another new second group into the output concealed data information sequence.

13. A method for processing data information in a system, for the purpose of concealing and protecting data information content, while simultaneously preserving part of the data information, segments of processed data information being contained within a system containing at least one data information, represented by electrical or wave signals or by data information existing in nature or in artificial databases or in storage media, where the processed data information is represented as a sequence of symbols selected out of a set consisting of characters, digits, or other arbitrary symbols, comprising the steps of:

partitioning the data information within a physical media or a machine, into short overlapping data information segments together having a number of symbols defining a size of the short overlapping data information segments, where the size of the short overlapping data information segments is at least identical or greater than a size of local data-information segments being studied, and wherein the local data information segments being studied are entirely contained within the short overlapping data information segments, these short overlapping data information segments constituting a first group;

modifying at least one short overlapping data information segment of the first group by pre-pending before or appending after at least one selected symbol, while said at least one selected symbol and a sequential order of said at least one selected symbol may repeat or differ, and an obtained mixture of the short overlapping data information segments and said modified at least one short overlapping data information segment of the first group constitutes a second group;

connecting segments of the second group into a sequence of data information;

partitioning the connected segments of the second group into short overlapping data information segments, this partitioning is carried out in such manner that, together with the partitioning of the connected segments of the first group, they result in an increased number of collections of at least three repeating data-information sub-segments being present within all segments of the output concealed data information, these short overlapping data information segments together having a number of symbols defining a size of the short overlapping data information segments, where the size of the short overlapping data information segments is at least identical or greater than a size of local data-information segments being studied, and wherein the local data information segments being studied are entirely contained within the short overlapping data information segments, these partitioned short overlapping data information segments constituting a new first group;

modifying at least one short overlapping data information segment of the new first group by prepending before or appending after at least one short data-information segment of the new first group at least one selected symbol, and an obtained mixture of the short data-information segments of the new first group and the modified short data-information segments of the new first group constituting a new second group;

connecting the segments of the new second group into a sequence of data information, this connecting is carried out in such manner that, together with the partitioning of the connected segments of the new first group, they result in an increased number of collections of at least three repeating data-information sub-segments being present within all segments of the output concealed data information;

partitioning the connected segments of the new second group into short overlapping data information segments, this partitioning is carried out in such manner that, together with the partitioning of the connected segments of the first group and together with the partitioning of the connected segments of the second group and together with connecting of the new second group into a sequence of data information, they result in an increased number of collections of at least three repeating data-information sub-segments being present within all segments of the output concealed data information, these short overlapping data information segments together having a number of symbols defining a size of the short overlapping data information segments, where the size of the short overlapping data information segments is at least identical or greater than a size of local data-information segments being studied, and wherein the local data information segments being studied are entirely contained within the short overlapping data information segments, these again partitioned short overlapping data information segments constituting another new first group; and modifying at least one short overlapping data information segment of the another new first group by prepending before or appending after at least one short data-information segment of the another new first group at least one selected symbol, and an obtained mixture of the short data-information segments of the another new first group and the modified short data-information segments of the another new first group constituting another new second group, connecting the segments of the another new second group into the output concealed data information sequence.

* * * * *